(12) United States Patent
Chhibber et al.

(10) Patent No.: US 8,373,859 B2
(45) Date of Patent: Feb. 12, 2013

(54) METHODS AND SYSTEMS FOR IMAGING SKIN USING POLARIZED LIGHTING

(75) Inventors: Rajeshwar Chhibber, San Jose, CA (US); Ashutosh Chhibber, San Jose, CA (US); Shefali Sharma, Petaluma, CA (US)

(73) Assignee: Brightex Bio-Photonics LLC, San Jose, CA (US)

( * ) Notice: Subject to any disclaimer, the term of this patent is extended or adjusted under 35 U.S.C. 154(b) by 373 days.

(21) Appl. No.: 12/731,072

(22) Filed: Mar. 24, 2010

(65) Prior Publication Data

US 2010/0245823 A1 Sep. 30, 2010

Related U.S. Application Data

(60) Provisional application No. 61/164,356, filed on Mar. 27, 2009.

(51) Int. Cl.
*G01J 4/00* (2006.01)
*G06K 9/62* (2006.01)

(52) U.S. Cl. ........ 356/366; 356/364; 356/367; 356/368; 382/165

(58) Field of Classification Search .......... 356/364–369; 348/77, 187, 211.3, 222.1, 370; 434/377, 434/99, 100, 371; 382/128, 165; 600/476, 600/410, 425
See application file for complete search history.

(56) References Cited

U.S. PATENT DOCUMENTS

| | | | |
|---|---|---|---|
| 4,151,512 A | 4/1979 | Riganati et al. | 340/146.3 E |
| 4,186,378 A | 1/1980 | Moulton | 340/146.3 E |
| 4,236,082 A | 11/1980 | Butler | 250/461 R |
| 4,871,262 A | 10/1989 | Krauss et al. | 366/160 |
| 4,894,547 A | 1/1990 | Leffell et al. | 250/461.2 |
| 5,074,306 A | 12/1991 | Green et al. | 128/664 |
| 5,343,536 A | 8/1994 | Groh | 382/6 |
| 5,363,854 A | 11/1994 | Martens et al. | 128/665 |
| 5,818,954 A | 10/1998 | Tomono et al. | 382/115 |
| 5,836,872 A | 11/1998 | Kenet et al. | 600/306 |
| 5,862,247 A | 1/1999 | Fisun et al. | 382/116 |
| 6,021,344 A | 2/2000 | Lui et al. | 600/476 |
| 6,032,071 A * | 2/2000 | Binder | 600/476 |
| 6,061,463 A | 5/2000 | Metz et al. | 382/124 |
| 6,069,689 A | 5/2000 | Zeng et al. | 356/73 |
| 6,081,612 A | 6/2000 | Gutkowicz-Krusin et al. | |
| 6,141,434 A | 10/2000 | Christian et al. | 382/103 |
| 6,317,624 B1 | 11/2001 | Kollias et al. | 600/476 |
| 6,475,153 B1 | 11/2002 | Khair et al. | 600/485 |
| 6,533,729 B1 | 3/2003 | Khair et al. | 600/503 |
| 6,556,708 B1 | 4/2003 | Christian et al. | 382/165 |
| 6,571,003 B1 | 5/2003 | Hillebrand et al. | 382/118 |

(Continued)

FOREIGN PATENT DOCUMENTS

WO    WO 90/13091    11/1990

OTHER PUBLICATIONS

International Search Report and Written Opinion for PCT/US2011/031065 dated Jun. 20, 2011, 11 pgs.

(Continued)

*Primary Examiner* — Sang Nguyen
(74) *Attorney, Agent, or Firm* — Morgan, Lewis & Bockius LLP

(57) ABSTRACT

An imaging system for imaging skin includes a light source to illuminate a subject and a first polarizer to polarize light provided by the light source to illuminate the subject. The imaging system also includes a photodetector to acquire an image of the subject as illuminated by the light source and an adjustable second polarizer, coupled to the photodetector, to provide an adjustable degree of polarization of light received by the photodetector.

8 Claims, 12 Drawing Sheets

U.S. PATENT DOCUMENTS

| | | | | |
|---|---|---|---|---|
| 6,587,711 | B1 | 7/2003 | Alfano et al. | 600/476 |
| 6,611,622 | B1 | 8/2003 | Krumm | 382/170 |
| 6,763,262 | B2 | 7/2004 | Hohla et al. | 600/476 |
| 6,782,307 | B2 | 8/2004 | Wilmott et al. | 700/233 |
| 7,217,266 | B2 * | 5/2007 | Anderson et al. | 606/12 |
| 7,233,693 | B2 | 6/2007 | Momma | 382/162 |
| 7,289,211 | B1 * | 10/2007 | Walsh et al. | 356/369 |
| 7,349,857 | B2 | 3/2008 | Manzo | 705/2 |
| 7,369,692 | B2 | 5/2008 | Shirai et al. | 382/128 |
| 7,454,046 | B2 | 11/2008 | Chhibber et al. | 382/128 |
| 7,460,248 | B2 | 12/2008 | Kurtz et al. | 356/521 |
| 7,477,767 | B2 | 1/2009 | Chhibber et al. | 382/128 |
| 7,840,064 | B2 | 11/2010 | Chhibber et al. | 382/165 |
| 2003/0223083 | A1 | 12/2003 | Geng | 356/603 |
| 2004/0111031 | A1 * | 6/2004 | Alfano et al. | 600/476 |
| 2004/0125996 | A1 | 7/2004 | Eddowes et al. | 382/128 |
| 2004/0179719 | A1 | 9/2004 | Chen et al. | 382/118 |
| 2004/0249274 | A1 | 12/2004 | Yaroslavsky et al. | 600/431 |
| 2005/0008199 | A1 | 1/2005 | Dong et al. | 382/115 |
| 2005/0046830 | A1 | 3/2005 | Karp et al. | 356/237.1 |
| 2005/0195316 | A1 | 9/2005 | Kollias et al. | 348/370 |
| 2006/0092315 | A1 | 5/2006 | Payonk et al. | 348/370 |
| 2006/0182323 | A1 | 8/2006 | Kollias et al. | 382/128 |
| 2007/0002479 | A1 | 1/2007 | Menke et al. | 359/892 |
| 2007/0004972 | A1 | 1/2007 | Cole et al. | 600/306 |
| 2007/0064978 | A1 | 3/2007 | Chhibber et al. | 382/118 |
| 2007/0064979 | A1 | 3/2007 | Chhibber et al. | 382/118 |
| 2008/0051773 | A1 | 2/2008 | Ivanov et al. | |
| 2008/0212894 | A1 | 9/2008 | Demirli et al. | |
| 2009/0136101 | A1 | 5/2009 | Chhibber et al. | 382/128 |
| 2009/0141956 | A1 | 6/2009 | Chhibber et al. | 382/128 |
| 2009/0196475 | A1 | 8/2009 | Demirli et al. | 382/128 |
| 2010/0309300 | A1 | 12/2010 | Chhibber et al. | 348/77 |
| 2010/0316296 | A1 | 12/2010 | Chhibber et al. | 382/190 |

OTHER PUBLICATIONS

Anonymous, *Build Your Own 3D Scanner w/Structured Light*, Nov. 23, 2009, 7 pgs.

Anonymous, *Stereo Accuracy and Error Modeling*, Point Grey Research Inc., Apr. 19, 2004, 3 pgs.

Basset, *Application of texture analysis for the classification of bovine meat*, Food Chemistry 69, 2000, pp. 437-445.

Blanz, *A Morphable Model for the Synthesis of 3D Faces*, SIGGRAPH '99, Losa Angeles CA, 1999, pp. 187-194.

Fulton, *Utilizing the Ultraviolet (UV Detect) Camera to Enhance the Appearance of Photodamage and Other Skin Conditions*, American Society for Dermatologic Surgery, 1997, pp. 163-169.

Hsu, *Face Detection in Color Images*, IEEE Transactions on Pattern Analysis and Machine Intelligence, vol. 24, No. 5, May 2002, pp. 696-706.

International Search Report and Written Opinion, PCT/2006/036696, Nov. 6, 2007, 5 pgs.

International Search Report and Written Opinion, PCT/2010/028617, May 20, 2010, 7 pgs.

Kollias, *Optical Non-Invasive Approaches to Diagnosis of Skin Diseases*, JID Symposium Proceedings, 2002, pp. 64-75.

Liangen, *Human Skin Surface Evaluation by Image Processing*, SPIE vol. 5254, 3rd Int'l Conference on Photonics and Imaging in Biology and Medicine, Bellingham WA, 2003, pp. 362-367.

Rosco color filter technical data sheet, 2001, 2 pgs.

Sandby-Moller, *Influence of epidermal thickness, pigmentation and redness on skin autofluorescence*, American Society of Photobiology, Jun. 2003, pp. 1-9.

Sboner, *Clinical validation of an automated system for supporting the early diagnosis of melanoma*, Skin Research and Technology, vol. 10, 2004, pp. 184-192.

Zeng, *Autofluorescence properties of skin and application in dermatology*, Proceedings of SPIE, Bol. 4224, 2000, pp. 366-373.

Zhang, *3-D Face Structure Extraction and Recognition From Images Using 3-D Morphing and Distance Mapping*, IEEE Transactions on Image Processing, vol. 11, No. 11, Nov. 2002, 1249-1259.

Brightex BIO-Photonics LLC, IPRP, PCT/US2011/031065, Oct. 11, 2012, 11 pgs.

* cited by examiner

Skin Condition Table
600

| | 604 | 606 | 608 | 610 | 612 |
|---|---|---|---|---|---|
| 602 | Name | Min. Color Value | Max. Color Value | Min. Intensity Value | Max. Intensity Value |
| Condition 1 | Name | Min. Color Value | Max. Color Value | Min. Intensity Value | Max. Intensity Value |
| Condition 2 | Name | Min. Color Value | Max. Color Value | Min. Intensity Value | Max. Intensity Value |

Figure 6A

Cosmetic Product Recommendation Table
630

| | 634 | 636 | 638 | 640 | 642 |
|---|---|---|---|---|---|
| 632 | Product | Min. Color Value | Max. Color Value | Min. Intensity Value | Max. Intensity Value |
| | Product | Min. Color Value | Max. Color Value | Min. Intensity Value | Max. Intensity Value |

Figure 6B

METHODS AND SYSTEMS FOR IMAGING SKIN USING POLARIZED LIGHTING

RELATED APPLICATIONS

This application claims priority to U.S. Provisional Patent Application No. 61/164,356, titled "Methods and Systems for Analyzing Skin Conditions Using Polarized Light," filed Mar. 27, 2009, which is hereby incorporated by reference in its entirety.

TECHNICAL FIELD

The disclosed embodiments relate generally to imaging and analyzing skin conditions, and more particularly, to imaging and analyzing skin conditions using polarized lighting.

BACKGROUND

High-quality images of a subject's skin have potential applications in dermatology and cosmetics, among other fields. Obtaining high-quality skin images, however, presents significant engineering challenges. For example, skin conditions on the surface of the skin, such as wrinkles, can interfere with imaging sub-surface features. In another example, skin care products can interfere with images taken using fluorescence techniques.

SUMMARY

In some embodiments, an imaging system for imaging skin includes a light source to illuminate a subject and a first polarizer to polarize light provided by the light source to illuminate the subject. The imaging system also includes a photodetector to acquire an image of the subject as illuminated by the light source and an adjustable second polarizer, coupled to the photodetector, to provide an adjustable degree of polarization of light received by the photodetector.

In some embodiments, a method of generating a sub-surface skin image includes illuminating a subject with polarized light having a first polarization. An adjustable polarizer is set to a first setting to admit light having the first polarization onto a photodetector and otherwise reject light. With the adjustable polarizer in the first setting, the photodetector is used to acquire a first image of the illuminated subject. The adjustable polarizer is set to a second setting to at least partially reject light having the first polarization and to at least partially admit light having polarization distinct from the first polarization onto the photodetector. With the adjustable polarizer in the second setting, the photodetector is used to acquire a second image of the illuminated subject. The first image is subtracted from the second image to generate a third image of the subject.

In some embodiments, a computer-implemented method of processing and displaying images of skin includes receiving a first image of a subject. The first image was acquired at an optical apparatus with the subject illuminated with light having a first polarization and the optical apparatus configured to receive light having the first polarization and to otherwise reject light. A second image of the subject is received. The second image was acquired at the optical apparatus with the subject illuminated with light having the first polarization and the optical apparatus configured to at least partially reject light having the first polarization and to at least partially receive light having polarization distinct from the first polarization. The first image is subtracted from the second image to generate a third image of the subject. The third image is displayed.

In some embodiments, a system for processing and displaying images of skin includes memory, a display, one or more processors, and one or more programs stored in the memory and configured for execution by the one or more processors. The one or more programs include instructions to receive a first image of a subject. The first image was acquired at an optical apparatus with the subject illuminated with light having a first polarization and the optical apparatus configured to receive light having the first polarization and to otherwise reject light. The one or more programs also include instructions to receive a second image of the subject. The second image was acquired at the optical apparatus with the subject illuminated with light having the first polarization and the optical apparatus configured to at least partially reject light having the first polarization and to at least partially receive light having polarization distinct from the first polarization. The one or more programs further include instructions to subtract the first image from the second image to generate a third image of the subject and instructions to display the third image.

In some embodiments, a computer readable storage medium stores one or more programs configured to be executed by a computer system to process and display images of skin. The one or more programs include instructions to receive a first image of a subject. The first image was acquired at an optical apparatus with the subject illuminated with light having a first polarization and the optical apparatus configured to receive light having the first polarization and to otherwise reject light. The one or more programs also include instructions to receive a second image of the subject. The second image was acquired at the optical apparatus with the subject illuminated with light having the first polarization and the optical apparatus configured to at least partially reject light having the first polarization and to at least partially receive light having polarization distinct from the first polarization. The one or more programs further include instructions to subtract the first image from the second image to generate a third image of the subject and instructions to display the third image.

BRIEF DESCRIPTION OF THE DRAWINGS

FIGS. 6A and 6B are diagrams illustrating data structures for analyzing images of skin in accordance with some embodiments.

Like reference numerals refer to corresponding parts throughout the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details. In other instances, well-known methods, procedures, components, and circuits have not been described in detail so as not to unnecessarily obscure aspects of the embodiments.

Figure 1:
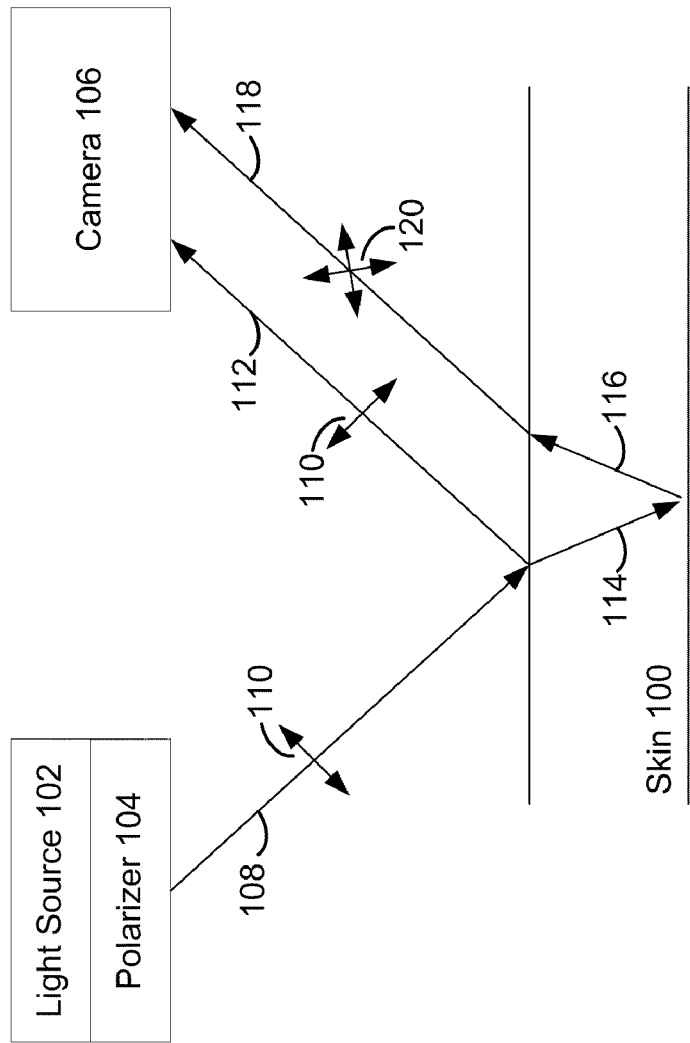
FIG. 1 is a schematic cross-sectional view of polarized light incident on and reflected from skin in accordance with some embodiments.

FIG. 1 is a schematic cross-sectional view of polarized light incident on and reflected from skin in accordance with some embodiments. A light source 102 is covered by a polarizer 104, such that light 108 illuminating skin 100 has a particular polarization 110. In the example of FIG. 1, the polarizer 104 is a linear polarizer and the light 108 is linearly polarized (i.e., polarization 110 is linear polarization). Light 112 is reflected from the surface of the skin 100 and detected by a camera (e.g., a digital camera) 106. The light 112 reflected from the surface of the skin 100 has the same polarization 110 as the incident light 108 and thus is also linearly polarized. Not all of the incident light 108 is reflected from the surface of the skin 100, however. A portion 114 of the incident light 108 penetrates to a particular depth within the skin 100 before being reflected. (For simplicity, FIG. 1 shows incident light 108 penetrating to a single depth within the skin before being reflected as light 116 and 118. In reality, incident light 108 penetrates to a range of depths before being reflected.) The light 118 reflected from beneath the surface of the skin 100 has a polarization (e.g., an elliptical polarization) 120 distinct from the polarization 110 of the light 112 reflected from the surface of the skin 100. In general, the polarization 120 of the light 118 is random.

The camera 106 thus receives partially polarized light: a portion of the received light has the polarization 110, and thus corresponds to light 112 reflected from the surface of the skin 100, while another portion has essentially random polarization 120, and thus corresponds to light 118 reflected from beneath the surface of the skin 100.

The camera 106 may be equipped with a polarizer which may be configured (e.g., by rotating the polarizer) to (1) admit only light having the polarization 110, such that all other polarizations are rejected, (2) reject all light having the polarization 110, such that admitted light is polarized perpendicular to the polarization 110, or (3) admit partially polarized light that includes components having the polarization 110 and components having a polarization perpendicular to the polarization 110. In the first case, an image taken by the camera 106 corresponds to light reflected from the surface of the skin 100 and is thus an image of the surface of the skin 100. In the second case, an image taken by the camera 106 corresponds to light reflected from a depth beneath the surface of the skin 100 that varies from approximately 350 microns for very dark skin to approximately 3 mm for very fair skin. The image in the second case is thus a sub-surface image of the skin 100. In the third case, an image taken by the camera 106 corresponds to light reflected from both the surface and from varying depths beneath the surface of the skin 100 and thus can be considered a combination of surface and sub-surface skin images.

Referring to the component of received light with the polarization 110 as PAR (i.e., polarized parallel to a plane of polarization of the incident light 108) and to the component of received light polarized perpendicular to the plane of polarization of the incident light 110 as PER, the degree of partial polarization of light admitted by the polarizer and thus imaged by the camera 106 can be quantified as:

$$\text{Degree of Partial Polarization} = (PAR - PER)/(PAR + PER) \quad (1)$$

This formula thus quantifies the percentage of light admitted by the polarizer that corresponds to light reflected from the surface of the skin 100 as opposed to light reflected from beneath the surface of the skin 100.

Figure 2A:
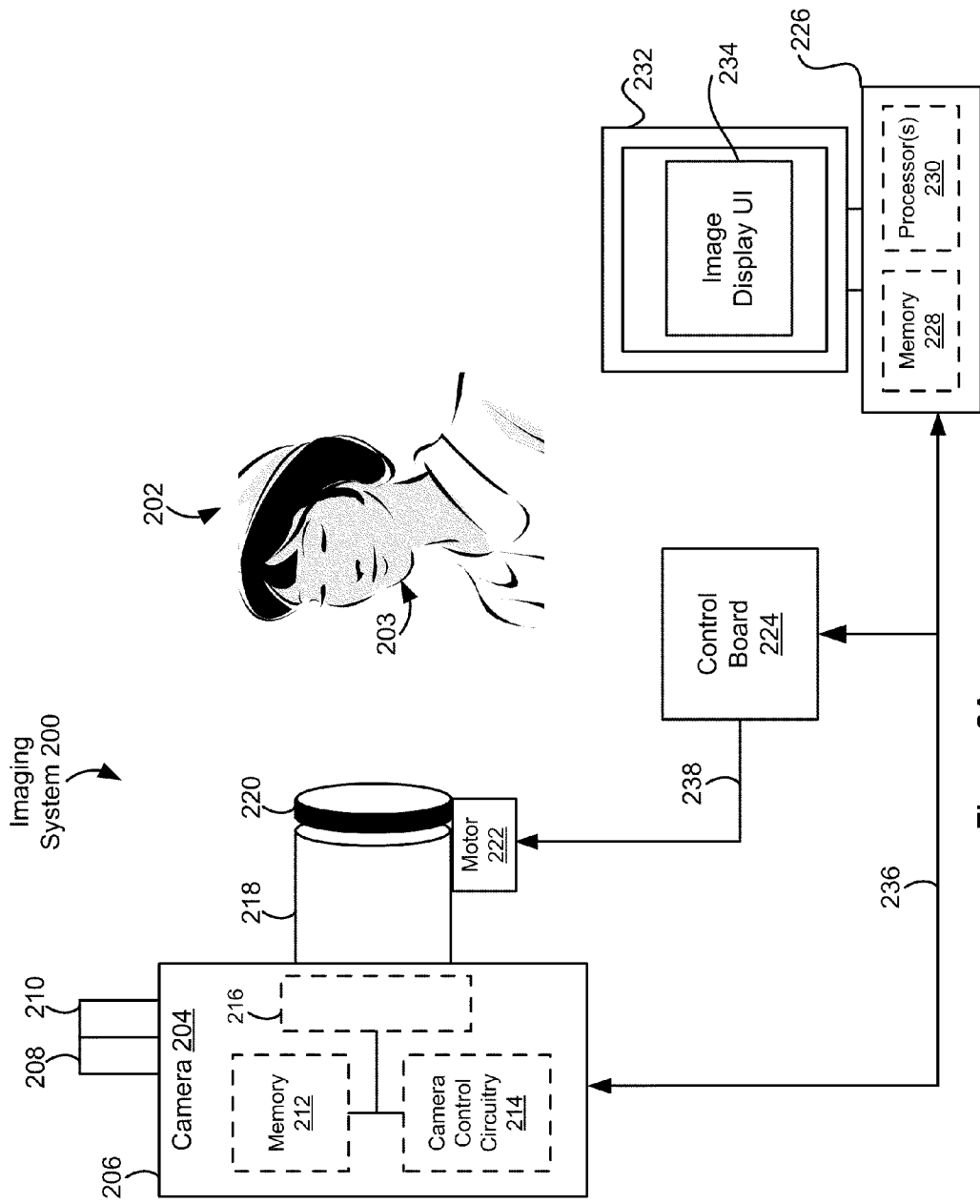
FIGS. 2A-2C are block diagrams of imaging systems for imaging skin in accordance with some embodiments.

FIG. 2A is a block diagram of an imaging system 200 for imaging skin 203 of a subject 202 in accordance with some embodiments. The imaging system 200 images the skin 203 in accordance with the physical principles illustrated in FIG. 1. While the system 200 is illustrated as imaging human facial skin, in some embodiments the system 200 may be used to image any type of animal skin. In the system 200, a camera (e.g., a digital camera) 204 includes a photodetector 216 to acquire images of the subject 202, computer memory 212 to store acquired images, and camera control circuitry 214 (e.g., one or more processors) to control acquisition and storage of the images. The photodetector 216, memory 212, and control circuitry 214 are contained in a housing 206 of the camera. In some embodiments, the photodetector 216 comprises an array of charge-coupled devices (CCD), charge-injection devices (i), or CMOS devices. In some embodiments, the photodetector 216 includes 5-15 or more megapixels. In some embodiments, each pixel includes three sub-pixels corresponding to three distinct color channels (e.g., red, green, and blue, or alternatively, a set of colors associated with another color space). In some embodiments, the photodetector 216 is rotatable to provide a variable aspect ratio for acquired images. Rotation of the photodetector 216 is controlled, for example, by the control circuitry 214.

The system 200 includes one or more light sources 208 (hereinafter, "light sources 208") to illuminate the subject 202 and one or more polarizers 210 (hereinafter, "polarizers 210") to polarize the light from the light sources 208 illuminating the subject 202. In some embodiments, the light sources 208 and polarizers 210 are coupled to the camera housing. For example, the light sources 208 and polarizers 210 may be affixed to the camera housing 206, as illustrated in FIG. 2A, or integrated into the camera housing 206. Alternatively, the light sources 208 and polarizers 210 may be physically separate from the camera 204. In some embodiments, the light sources 208 include one or more flash bulbs, one or more light-emitting diodes (LEDs), or one or more fluorescent high-temperature white-light sources. In some embodiments, the polarizers 210 include one or more linear polarizers. If multiple polarizers 210 are present, the multiple polarizers 210 are aligned to provide the same polarization. In some embodiments, the polarizers 210 are fixed, such that the polarization they provide is not adjustable. A polarizer 210 may be mounted on a respective light source 208 or otherwise arranged such that it polarizes light from the light source 208 that is incident on the subject 202.

The camera 204 includes a lens 218 to focus light onto the photodetector 216. In some embodiments the lens 218 is a zoom lens that provides variable heightened image resolution. The zoom lens may be motorized and controlled by associated control circuitry (e.g., included in the control circuitry 214) or may be manually adjustable. The high resolution provided by a zoom lens enables accurate measurement of imaged skin features (e.g., pore size, hair strands, hair follicles, spots, and moles).

An adjustable polarizer 220 is rotatably mounted on the lens 218 and thereby coupled to the photodetector. In some embodiments, the polarizer 220 is an elliptical polarizer, or a circular polarizer, or a linear polarizer. Rotating the polarizer 220 provides an adjustable degree of polarization of light received by the photodetector 216. In some embodiments, a motor 222 attached to the polarizer 220 rotates the polarizer 220 (e.g., in defined angular increments) in response to instructions from polarizer control circuitry on a control board 224 coupled to the motor 222 via one or more signal lines 238. Alternatively, a knob 242 allows manual adjustment of a degree of rotation of the polarizer 220, as illustrated in the imaging system 240 (FIG. 2B) in accordance with some embodiments.

The polarizer 220 may be adjusted such that it is aligned with the polarizers 210 and thus only admits light with the same polarization as light from the light sources 208 as filtered by the polarizers 210. In this configuration, the polarizer 220 is said to have 0° rotation with respect to the polarizers 210. With the polarizer 220 in this configuration, the photodetector 216 may acquire an image of the subject 202 corresponding to light reflected from the surface of the subject's skin 203.

The polarizer 220 may be adjusted such that it is rotated 90° with respect to the polarizers 210. In this configuration, the polarizer 220 rejects all light with the polarization provided by the polarizers 210 and admits light having a perpendicular polarization. With the polarizer 220 in this configuration, the photodetector 216 may acquire a sub-surface skin image of the subject 202 (e.g., corresponding to light reflected from a depth beneath the surface of the subject's skin 203 that varies from approximately 350 microns for very dark skin to approximately 3 mm for very fair skin).

The polarizer 220 may be adjusted such that it is rotated between 0° and 90° with respect to the polarizers 210. In this configuration, the polarizer 220 admits partially polarized light in accordance with Equation (1). With the polarizer 220 in this configuration, the photodetector 216 may acquire an image of the subject 202 corresponding to a combination of surface and sub-surface skin images. This image may be processed to produce a sub-surface skin image by subtracting an image taken with 0° rotation of the polarizer 220.

In some embodiments, an imaging system includes a light shield 252 to shield the subject 202 from ambient light, as illustrated for the imaging system 250 (FIG. 2C) in accordance with some embodiments. In the system 250, the camera 204 is mounted on a back wall of the light shield 252, which extends outward from the camera housing 208 with a frusto-conical shape. By shielding the subject 202 from ambient light, the light shield ensures that most of the light reflected from the subject 202 and received at the photodetector 216 originated from the light sources 208 and was filtered by the polarizers 210.

A computer 226 (FIGS. 2A-2B) is coupled to the camera 204 and control board 224 via one or more signal lines 236. The computer 226 includes memory 228 and one or more processors 230 as well as a monitor 232 for displaying a user interface (UI) 234. The UI 234 displays acquired and/or processed images as well as data calculated from acquired and/or processed images. In some embodiments, the computer 226 provides instructions to the control board 224 to rotate the polarizer 220, instructions to the camera 204 to adjust the zoom lens 218, and instructions to the camera 204 to acquire an image (i.e., to take a picture). The computer 800 (FIG. 8, below) illustrates an example of an implementation of the computer 226 in accordance with some embodiments.

In some embodiments, the functionality of the computer 226 is integrated into the camera 204. In some embodiments, the camera 204 includes a display for viewing acquired and/or processed images as well as data calculated from acquired and/or processed images.

Figure 3:
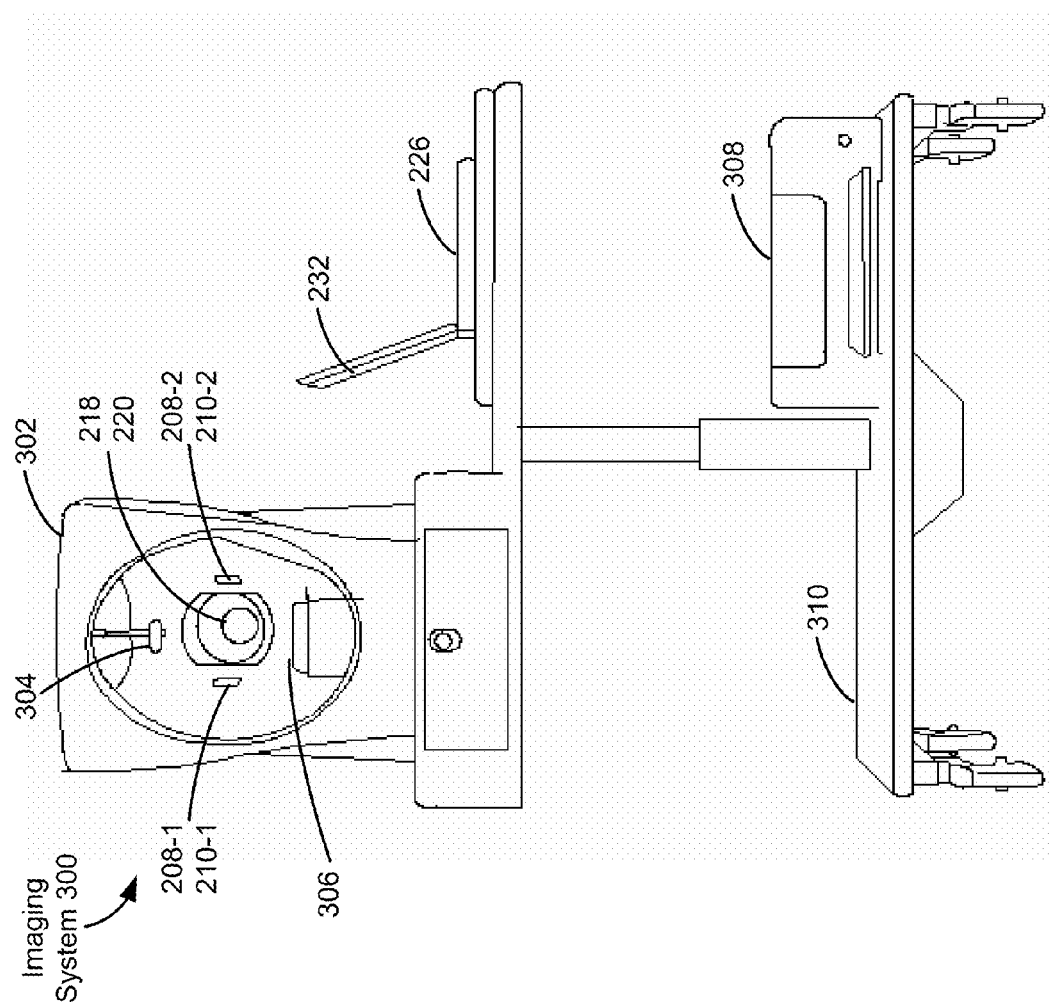
FIG. 3 is a diagram illustrating an imaging system including a light box in accordance with some embodiments.

In some embodiments, the light sources 208, polarizers 210, and camera 204 (including polarizer 220) are mounted in an imaging box 302, as illustrated for the imaging system 300 (FIG. 3). The imaging box 302, shown as mounted on a cart 310 for mobility, serves as a light shield to shield the subject from ambient light. First and second light sources 208-1, 208-2 and first and second polarizers 210-1, 210-2 are mounted on a rear wall of the box 302, opposite from a chin rest 306 and forehead pad 304 for receiving the subject's head. An example of such an imaging box 302 is the Facial Stage DM-3 commercially available from Moritex Corporation of Tokyo, Japan. The system 300 also includes a printer 308 for printing acquired and/or processed images as well as data calculated from acquired and/or processed images.

In some embodiments, a reference material is included in acquired images to measure light source intensity output change and color change over time (e.g., resulting from drift in a light source 208). For example, a standard color chart such as the GretagMacbeth ColorChecker may be placed in the field of imaging (e.g., beneath the chin of the subject 202) and used to calibrate the photodetector 216 and/or to post-process acquired images to adjust pixel values based on comparison to known pixel values for colors in the color chart. Furthermore, image processing software may be used to correct for optical aberrations.

Skin pixels in surface or sub-surface skin images (e.g., images generated using an imaging system 200, 240, 250, or 300, FIGS. 2A-2C and 3) may be analyzed to identify at least one skin condition by comparing pixel values to predetermined criteria associated with various skin conditions. Conditions associated with the skin that may be detected and classified include, but are not limited to, skin tone/color, pigment evenness, pigment darkness, diffuse redness (e.g., indicative of sensitive or reactive skin), intense localized red levels (e.g., indicative of vascular lesions/telangiectasias), radiance intensity, enlarged pores, roughness variation, emerging lines, fine lines, wrinkles, UV damage, pore health, hydration levels, collagen content, skin type, topical inflammation or recent ablation, keratosis, deeper inflammation, sun spots, different kinds of pigmentation including freckles, moles, growths, undereye circles, scars, acne, fungi, erythema and other artifacts. In addition, image pixels may be used to perform feature measurements, such as the size or volume of a lip, nose, eyes, ears, chin, cheeks, forehead, eyebrows, teeth, or other features. Other examples of feature measurements, including pore size measurements, spot counts, and measurement of the length, thickness and/or curvature of an eyelash, can be made based on information from image pixels. Image pixels may be used to characterize lip conditions, which may include, without limitation, lip surface area, color, fine lines, wrinkles, and characteristics associated with lip edge demarcation. Characteristics associated with lip edge demarcation may include, for example, color contrast, line roughness, and color variation.

In some embodiments, a skin condition look-up table 600 (FIG. 6A) is used to identify skin conditions. A color value and an intensity value is measured for a respective skin pixel or group of skin pixels and compared against color and intensity values for various skin conditions as stored in the table 600. The table 600 includes a row 602 for each respective skin condition stored in the table 600. Each row includes fields that specify a name 602 of a respective skin condition as well as the minimum color value 606, maximum color 608, minimum intensity value 610, and maximum intensity value 612 associated with the respective skin condition. If the measured color and intensity values match the values specified in a row 602, the respective skin condition corresponding to the row is identified.

In some embodiments, to analyze either skin pixels or non-skin pixels (e.g., pixels corresponding to hair, clothing, eyes, lips, etc.) in surface or sub-surface skin images, pixels are analyzed on a pixel-by-pixel basis to distinguish skin pixels from non-skin pixels. Identification of skin and non-skin pixels is described, for example, in U.S. Pat. No. 7,454,046, entitled "Method and System for Analyzing Skin Conditions Using Digital Images," issued Nov. 18, 2008, which is hereby incorporated by reference herein in its entirety. For example, assuming the pixels have red, green, and blue sub-pixels with pixel values that range between 0-255, pixels with red channel values in the range of 105-255, green channel values in the range of 52-191, and blue channel values in the range of 32-180 are identified as skin pixels. Furthermore, in some embodiments a pre-stored template or coordinate reference is used to define certain pixels as non-skin pixels and a skin map or skin mask may be used to define certain pixels as non-skin pixels, as described in U.S. Pat. No. 7,454,046 in accordance with some embodiments.

In some embodiments, a surface skin image is compared to a sub-surface skin image to compare surface and sub-surface skin conditions. For example, surface and sub-surface pigmentation may be compared.

In some embodiments, a sub-surface image may be used alone to analyze pigmentation or other skin conditions. Sub-surfaces images exclude wrinkles on the surface of the skin, which can interfere with imaging of pigmentation. Sub-surface images also exclude glare from the surface of the skin, which also can interfere with imaging of pigmentation and other skin features or conditions. Accordingly, sub-surface images can provide a more accurate indication of skin tone or color than surface images, and can provide a more accurate indication of other skin conditions as well.

In some embodiments, images (either surface or sub-surface) generated by an imaging system (e.g., an imaging system 200, 240, 250, or 300, FIGS. 2A-2C and 3) are compared with old (i.e., historical) images stored in memory to identify variations in skin conditions and features over time. For example, a newly generated image may be displayed next to a stored historical image in a user interface (e.g., UI 234, FIGS. 2A-2B). A computer system (e.g., the computer 226, FIGS. 2A-2B) performs automated comparison of one or more newly generated images with one or more historical images to track changes in skin conditions and features. For example, the system calculates changes in pigmentation (e.g., skin tone) and changes in size or color of features on the skin. Results of this automated comparison are displayed in a user interface (e.g., UI 234, FIGS. 2A-2B).

When comparing multiple images, the images are first aligned to allow the same features to be identified in the multiple images. In some embodiments, images are aligned using a three-point selection process that identifies points in the center of the eyes and the center of the lips and aligns the images accordingly.

Figure 4:
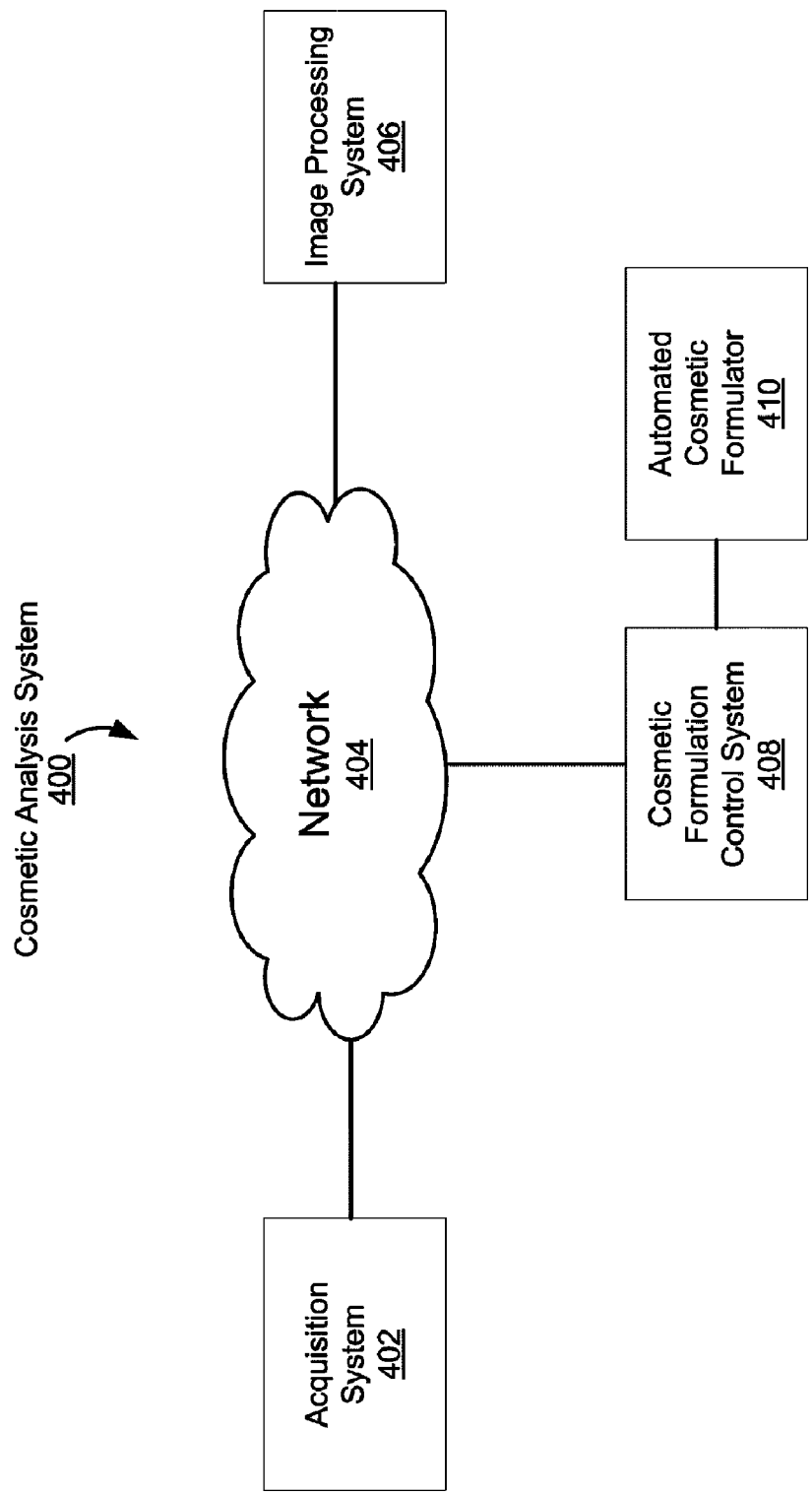
FIG. 4 is a block diagram illustrating a system in which a network couples an acquisition system to an image processing system and a cosmetic formulation system in accordance with some embodiments.

In the imaging systems 200, 240, and 300 (FIGS. 2A-2B and 3) the computer 226 is directly connected to the camera 204. In some embodiments, however, an acquisition system 402 that includes a camera 204 is coupled to an image processing system 406 through a network 404. FIG. 4 is a block diagram illustrating a system 400 in which a network 404 couples an acquisition system 402 to an image processing system 406 in accordance with some embodiments. The network 404 may be any suitable wired and/or wireless network and may include a local area network (LAN), wide area network (WAN), virtual private network (VPN), the Internet, metropolitan area network (MAN), or any combination of such networks. The image processing system 406 may perform various types of processing related to images acquired by the acquisition system, including without limitation subtracting a first image from a second image to generate a sub-surface image, analyzing pixel data to identify skin or feature conditions, and comparing images.

In some embodiments, a system such as the computer 226 (FIG. 2A-2B) or image processing system 406 (FIG. 4) generates a recommendation for a cosmetic product based on analysis of skin pixels. For example, the system may analyze skin color in a sub-surface image and recommend a cosmetic product based on the skin color. In some embodiments, the recommendation is displayed to the subject 202 (e.g., in the UI 234, FIGS. 2A-2B) or printed out (e.g., using the printer 308, FIG. 3). In some embodiments, the recommendation is provided at the point of sale (POS) where the subject may buy the recommended product or is displayed on a web page that the subject may use to order the recommended product.

In some embodiments, the image processing system 406 (or alternatively the acquisition system 402) transmits the recommendation (e.g., through the network 404) to a cosmetic formulation control system 408 coupled to an automated cosmetic formulator 410. The formulator 410 then prepares the recommended product in real time, thus providing the subject with a customized cosmetic product based on the recommendation.

In some embodiments, the image processing system 406 and cosmetic formulation control system 408 are integrated into a single system.

Figure 5:
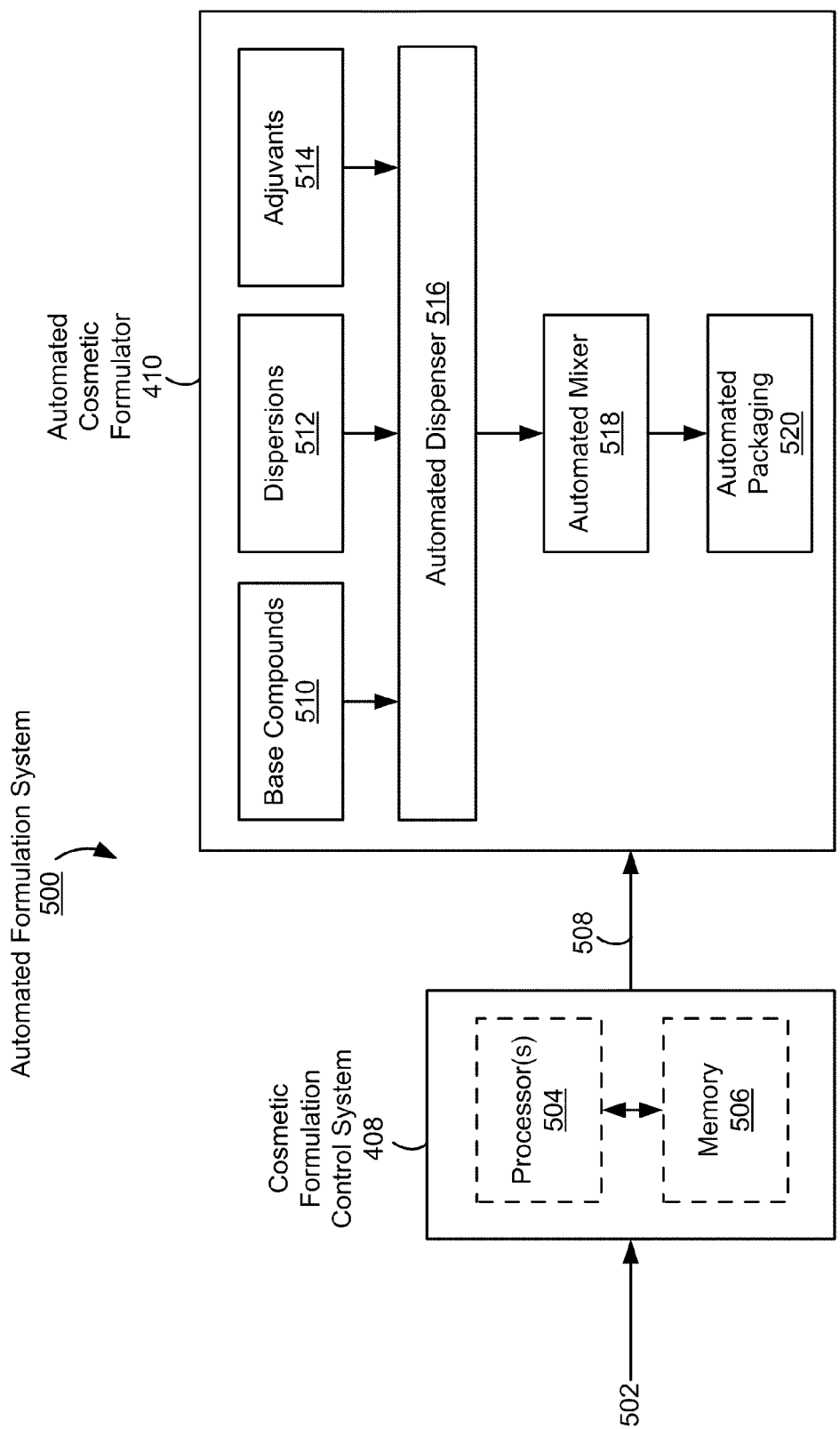
FIG. 5 is a block diagram illustrating an automated formulation system that includes a cosmetic formulation control system coupled to an automated cosmetic formulator in accordance with some embodiments.

FIG. 5 is a block diagram illustrating an automated formulation system 500 that includes a cosmetic formulation control system 408 coupled to an automated cosmetic formulator 410 in accordance with some embodiments. The control system 408, which includes memory 506 and one or more processors 504, receives a recommendation for a customized cosmetic product through a network connection 502. Based on the recommendation, the control system 408 determines a formula for the customized cosmetic product (e.g., using a look-up table stored in the memory 506) and provides instructions to the automated cosmetic formulator 410 via one or more signal lines 508 to mix the customized cosmetic product. Alternatively, the formula is provided to the system 500 in the recommendation. An automated dispenser 516 in the formulator 410 dispenses one or more base compounds 510, dispersions 512, and adjuvants 514 to an automated mixer 518 in accordance with the formula. The mixer 518 mixes the base compounds 510, dispersions 512, and adjuvants 514 and provides the mixture to an automated packaging unit 520, which packages the mixture and dispenses it. In some embodiments, the system 500 is located at the POS. Alternatively, the customized cosmetic product provided by the system 500 may be shipped to the customer.

FIG. 6B is a diagram illustrating a data structure of a cosmetic product recommendation table 630 used to generate a recommendation for a cosmetic product based on analysis of skin pixels. A color value and an intensity value is measured for a respective skin pixel or group of skin pixels and compared against color and intensity values for various cosmetic products as stored in the table 630. The table 630 includes a row 632 for each respective cosmetic product stored in the table 630. Each row 632 includes fields that specify a respective cosmetic product 634 as well as the minimum color value 636, maximum color 638, minimum intensity value 640, and maximum intensity value 642 associated with the respective skin condition. If the measured color and intensity values match the values specified in a row 632, the respective cosmetic product corresponding to the row is recommended.

Figure 7A:
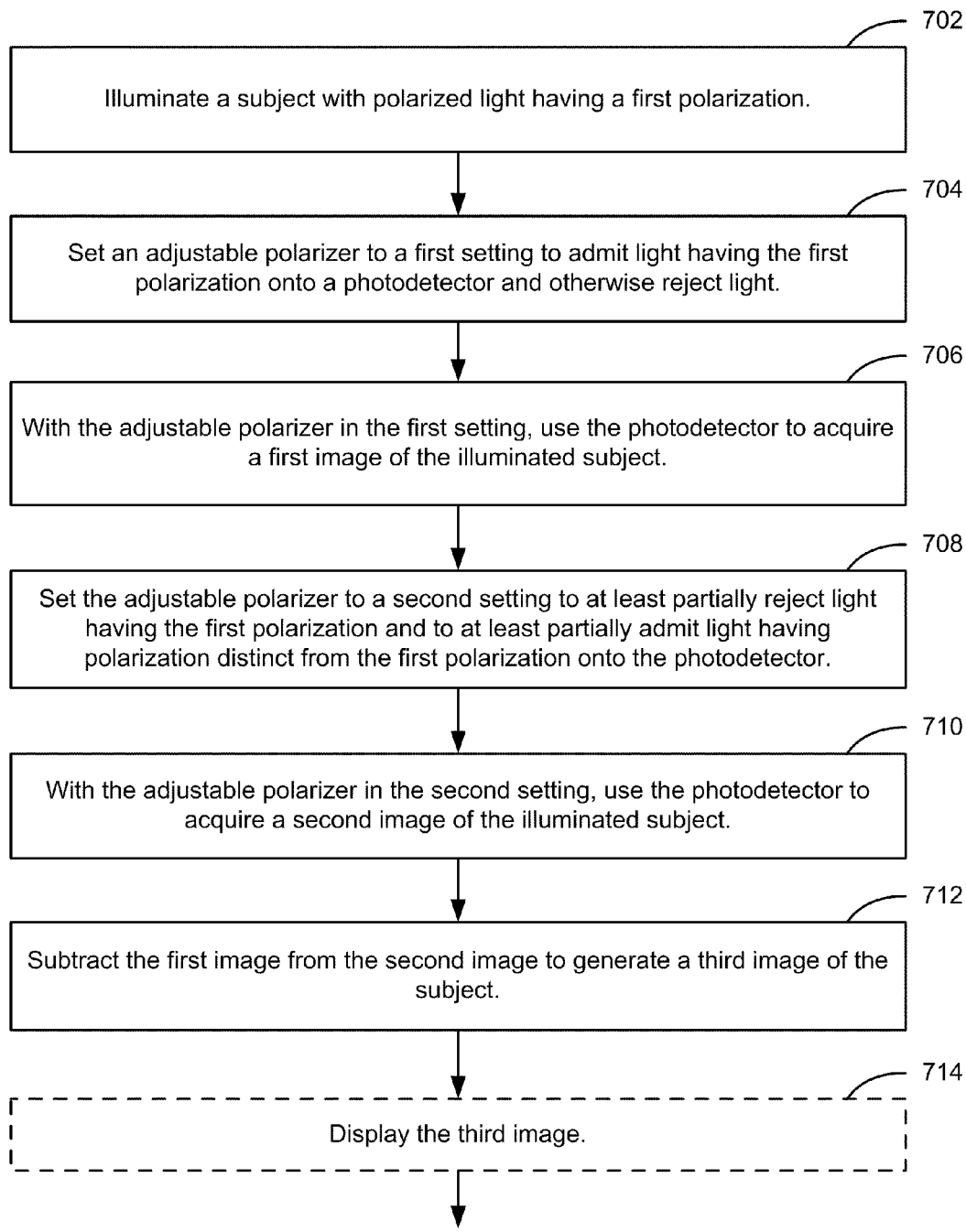
FIGS. 7A-7C are flow diagrams illustrating a method of generating a sub-surface skin image in accordance with some embodiments.

FIG. 7A is a flow diagram illustrating a method 700 of generating a sub-surface skin image in accordance with some embodiments. In the method 700, a subject is illuminated (702) with polarized light having a first polarization. For example, the subject 202 (FIGS. 2A-2C) is illuminated using light from one or more light sources 208 as filtered by one or more polarizers 210.

An adjustable polarizer (e.g., polarizer 220, FIGS. 2A-2C) is set (704) to a first setting (e.g., a 0° rotation with respect to the polarizers 210) to admit light having the first polarization onto a photodetector (e.g., photodetector 216, FIGS. 2A-2C) and otherwise reject light. With the adjustable polarizer in the first setting, the photodetector is used (706) to acquire a first image of the illuminated subject. The first image thus corresponds to light reflected from the surface of the subject's skin.

The adjustable polarizer is set (708) to a second setting to at least partially reject light having the first polarization and to at least partially admit light having polarization distinct from the first polarization onto the photodetector. The second setting thus corresponds to a degree of rotation greater that 0° with respect to the polarizers 210. With the adjustable polarizer in the second setting, the photodetector is used (710) to acquire a second image of the illuminated subject. The second image thus at least partially includes sub-surface image data.

The first image is subtracted (712) from the second image to generate a third image of the subject. This subtraction is performed, for example, by the computer 226 (FIGS. 2A-2B) or by the image processing system 406 (FIG. 4). Because the first image is a surface image and the second image at least partially includes sub-surface image data, subtracting the first image from the second image produces a sub-surface image. The third image thus is a sub-surface image of the subject's skin. In some embodiments, if the second setting completely rejects light having the first polarization, the subtraction operation 712 is omitted, since the second image already is a sub-surface image.

Figure 2B:
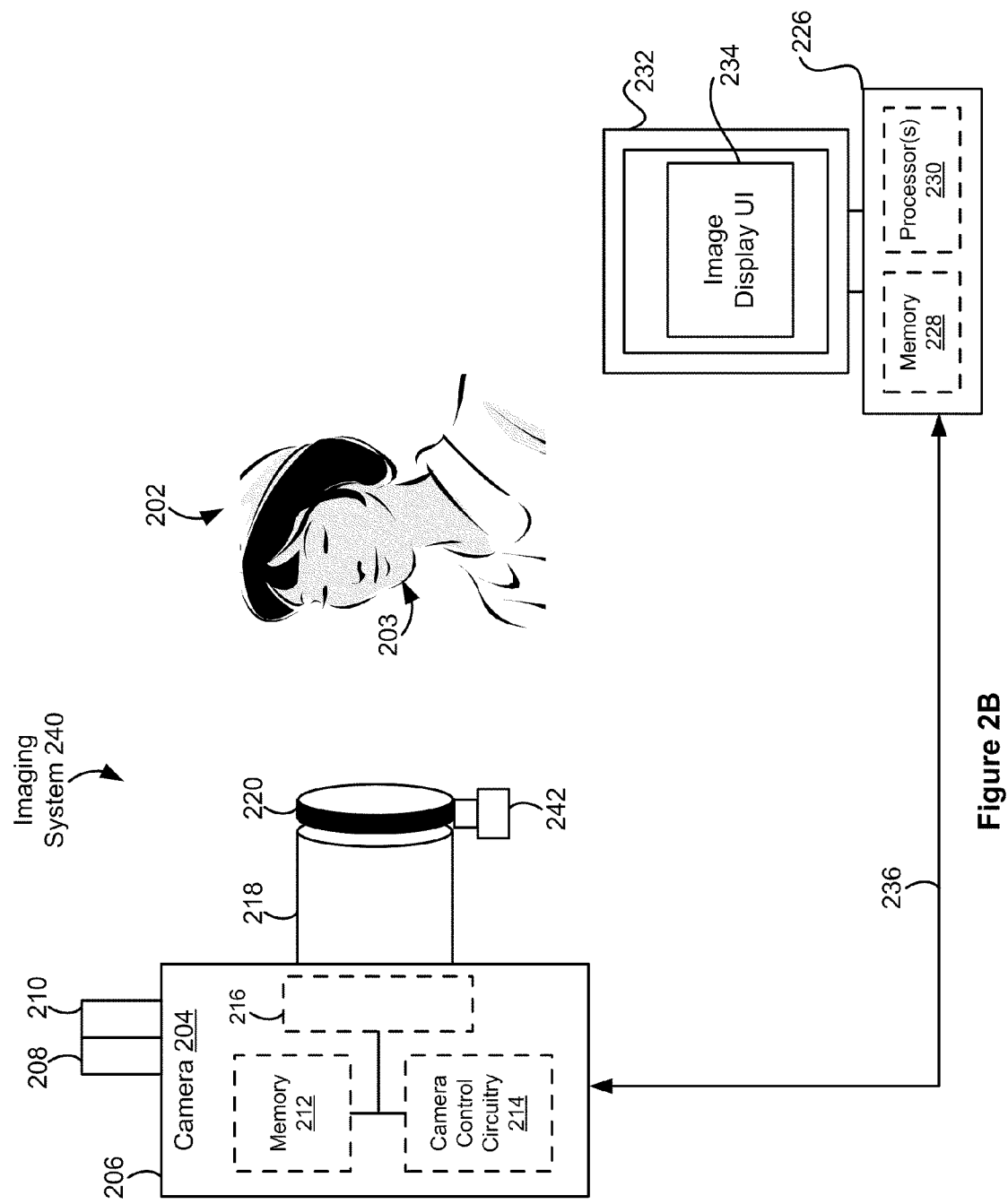

In some embodiments, the third image is displayed (714) (e.g., in the UI 234, FIGS. 2A-2B). In some embodiments, the third image is analyzed and results of the analysis are displayed (e.g., in the UI 234, FIGS. 2A-2B).

Figure 7B:
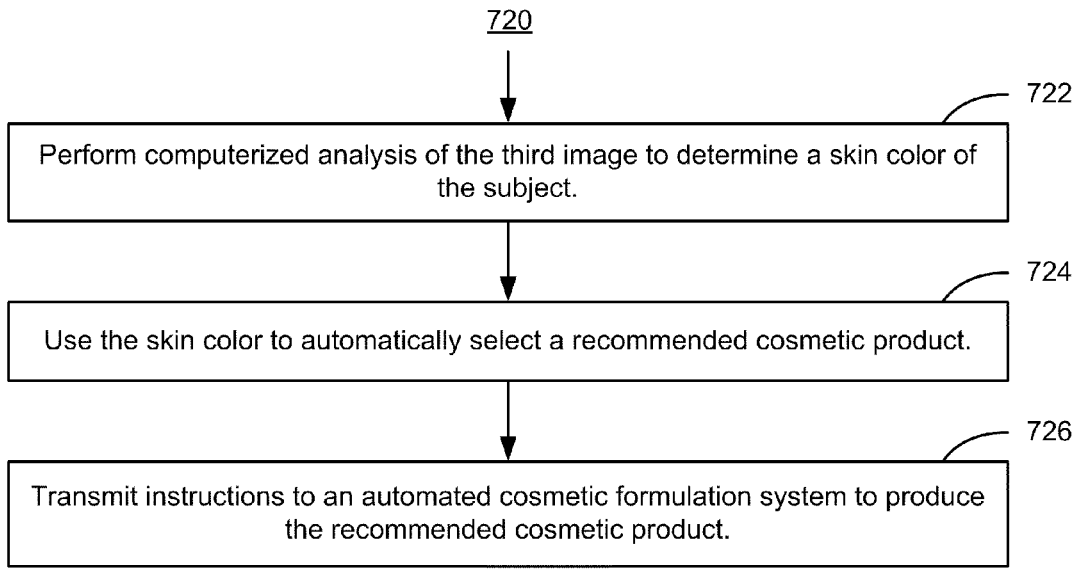

In some embodiments, the method 700 further includes a method 720 as illustrated in FIG. 7B in accordance with some embodiments. In the method 720, a computerized analysis is performed (722) of the third image to determine a skin color of the subject. The skin color is used to automatically select (724) a recommended cosmetic product. Instructions are transmitted (726) to an automated cosmetic formulation system (e.g., the system 500, FIG. 5) to produce the recommended cosmetic product. The method 720 is performed, for example, by the computer 226 (FIGS. 2A-2B) or by the image processing system 406 (FIG. 4).

Figure 7C:
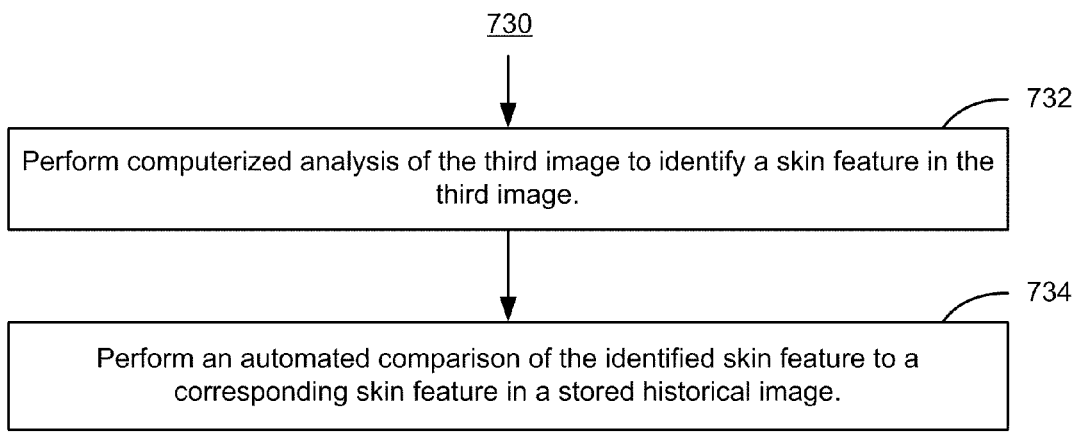

In some embodiments, the method 700 further includes a method 730 as illustrated in FIG. 7C in accordance with some embodiments. In the method 730, a computerized analysis of the third image is performed (732) to identify a skin feature (e.g., a skin condition) in the third image. An automated comparison of the identified skin feature to a corresponding skin feature in a stored historical image is performed (734). Results of the comparison are displayed (e.g., in the UI 234, FIGS. 2A-2B). The method 730 is performed, for example, by the computer 226 (FIGS. 2A-2B) or by the image processing system 406 (FIG. 4).

In some embodiments, the photodetector is calibrated (e.g., using a color chart positioned in the field of image) and the first and second images are corrected in accordance with the calibration.

Figure 7D:
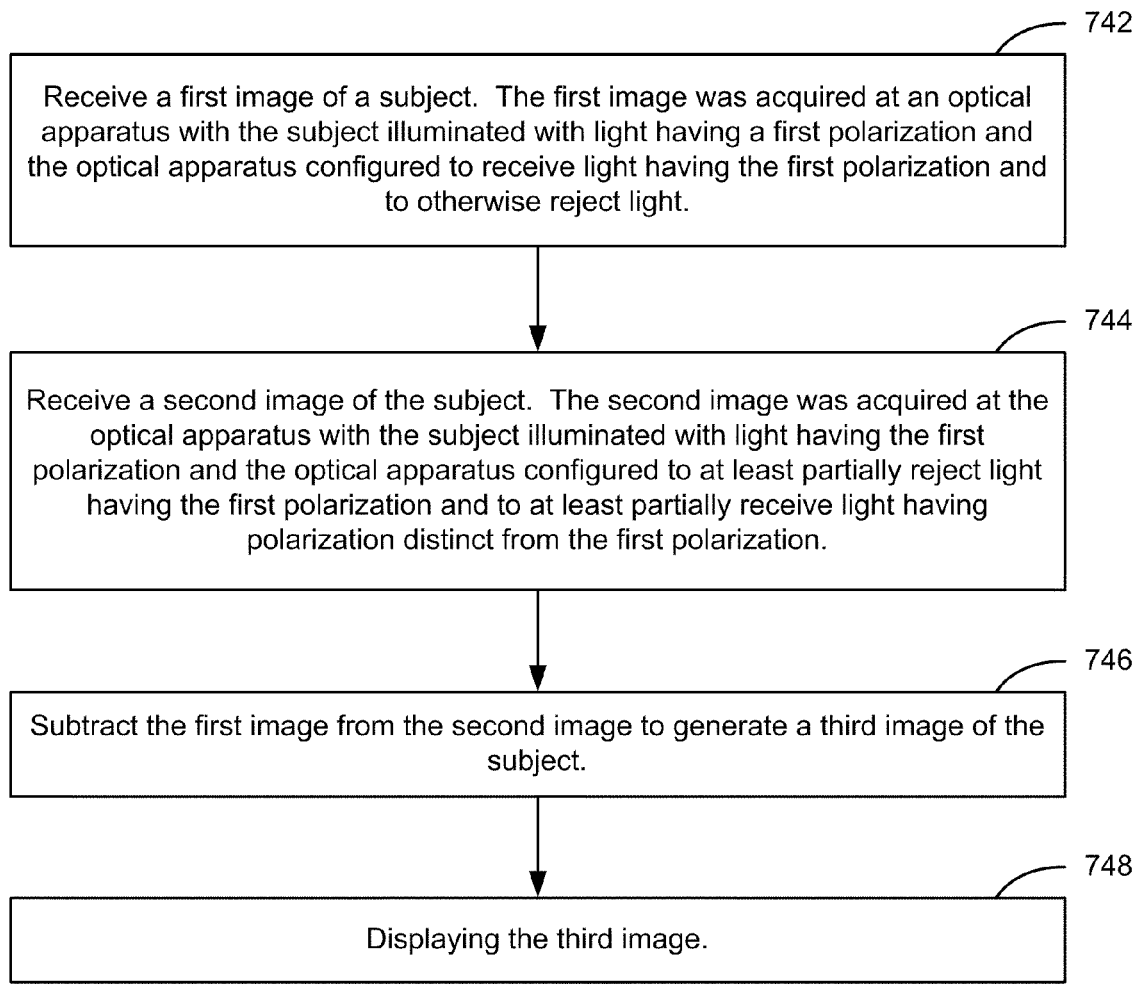
FIG. 7D is a flow diagram illustrating a computer-implemented method of processing and displaying images of skin in accordance with some embodiments.

FIG. 7D is a flow diagram illustrating a method 740 of processing and displaying images of skin in accordance with some embodiments. The method 740 is implemented at a computer system such as the computer 226 (FIGS. 2A-2B) or the image processing system 406 (FIG. 4).

In the method 740, a first image of a subject (e.g., subject 202, FIGS. 2A-2C) is received (742). The first image was acquired at an optical apparatus (e.g., a camera 204, FIGS. 2A-2C) with the subject illuminated with light having a first polarization (e.g., light from one or more light sources 208 as filtered by one or more polarizers 210, FIGS. 2A-2C). The first image was acquired with the optical apparatus configured to receive light having the first polarization and to otherwise reject light (e.g., an adjustable polarizer 220 was set to a 0° rotation with respect to the polarizers 210).

A second image of the subject is received (744). The second image was acquired at the optical apparatus with the subject illuminated with light having the first polarization. The second image was acquired with the optical apparatus configured to at least partially reject light having the first polarization and to at least partially receive light having polarization distinct from the first polarization (e.g., an adjustable polarizer 220 was set to a rotation of greater than 0° with respect to the polarizers 210).

The first image is subtracted (746) from the second image to generate a third image of the subject. The third image is displayed (748). In some embodiments, the third image is analyzed to identify skin conditions or features and results of the analysis are displayed.

Figure 8:
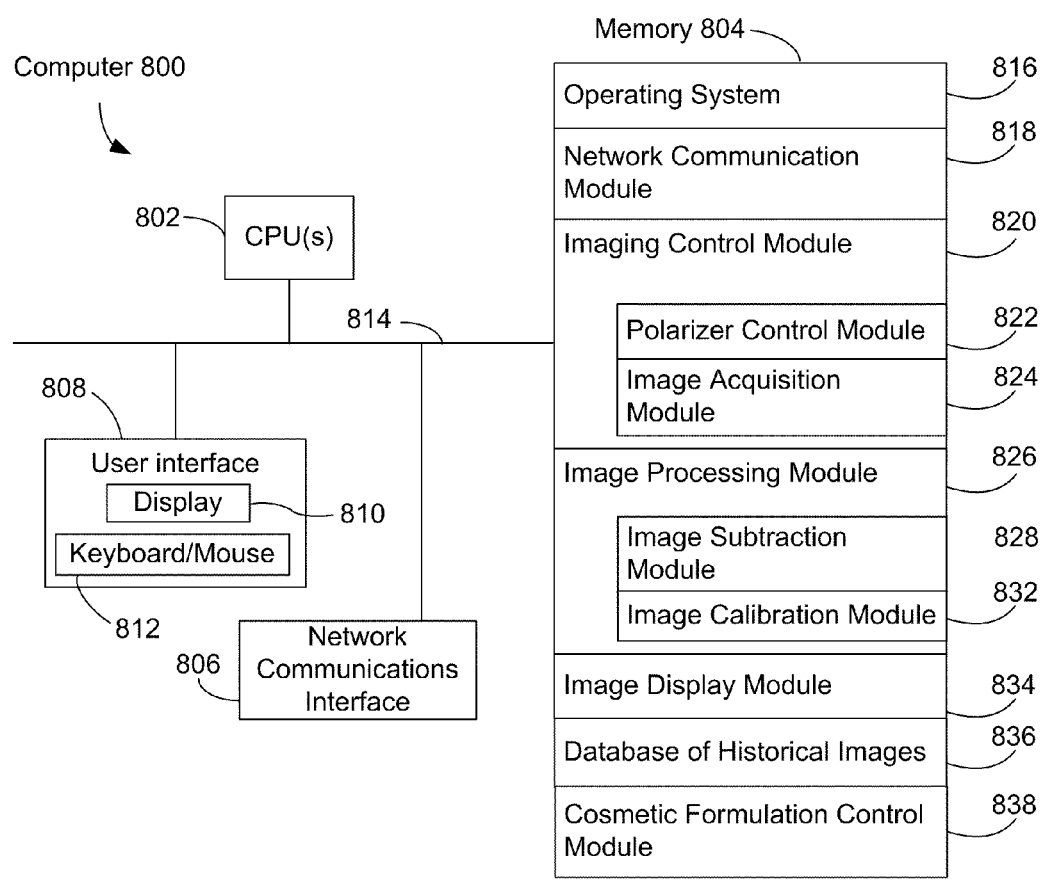
FIG. 8 is a block diagram illustrating a computer in accordance with some embodiments.

FIG. 8 is a block diagram illustrating a computer 800 in accordance with some embodiments. In some embodiments the computer 800 is an example of an implementation of the computer 226 (FIGS. 2A-2B), image processing system 406 (FIG. 4), or cosmetic formulation control system 408 (FIG. 4). The computer 800 typically includes one or more central processing units (CPUs) 802, one or more network or other communications interfaces 806, memory 804, and one or more communication buses 814 for interconnecting these components. The communication buses 814 may include circuitry (sometimes called a chipset) that interconnects and controls communications between system components. The computer 800 may also include user interface hardware 808 comprising a display device 810 and a keyboard and/or mouse (or other pointing device) 812. Memory 804 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 804 may optionally include one or more storage devices remotely located from the CPU(s) 802. Memory 804, or alternately non-volatile memory device(s) within memory 804, comprises a computer readable storage medium. In some embodiments, memory 804 stores instructions for performing all or a portion of the methods 700, 720, 730, and/or 740 (FIGS. 7A-7D). In some embodiments, memory 804 stores the following programs, modules, and data structures, or a subset thereof:

an operating system 816 that includes procedures for handling various basic system services and for performing hardware dependent tasks;

a network communication module 818 that is used for connecting the computer 800 to other computers via the one or more communication network interfaces 806 and one or more communication networks, such as the Internet, other wide area networks, local area networks, metropolitan area networks, and so on;

an imaging control module 820 for controlling an imaging system (e.g., a system 200, 240, 250, or 300, FIGS. 2A-2C and 3);

an image processing module 826 to process acquired skin images (e.g., images acquired using a system 200, 240, 250, or 300, FIGS. 2A-2C and 3);

an image display module 834 module to display skin images and data corresponding to skin images;

a database of historical images 836 (e.g., for comparison to newly acquired images); and a cosmetic formulation control module 838 for controlling an automated cosmetic formulator (e.g., formulator 48, FIGS. 4 and 5).

Figure 2C:
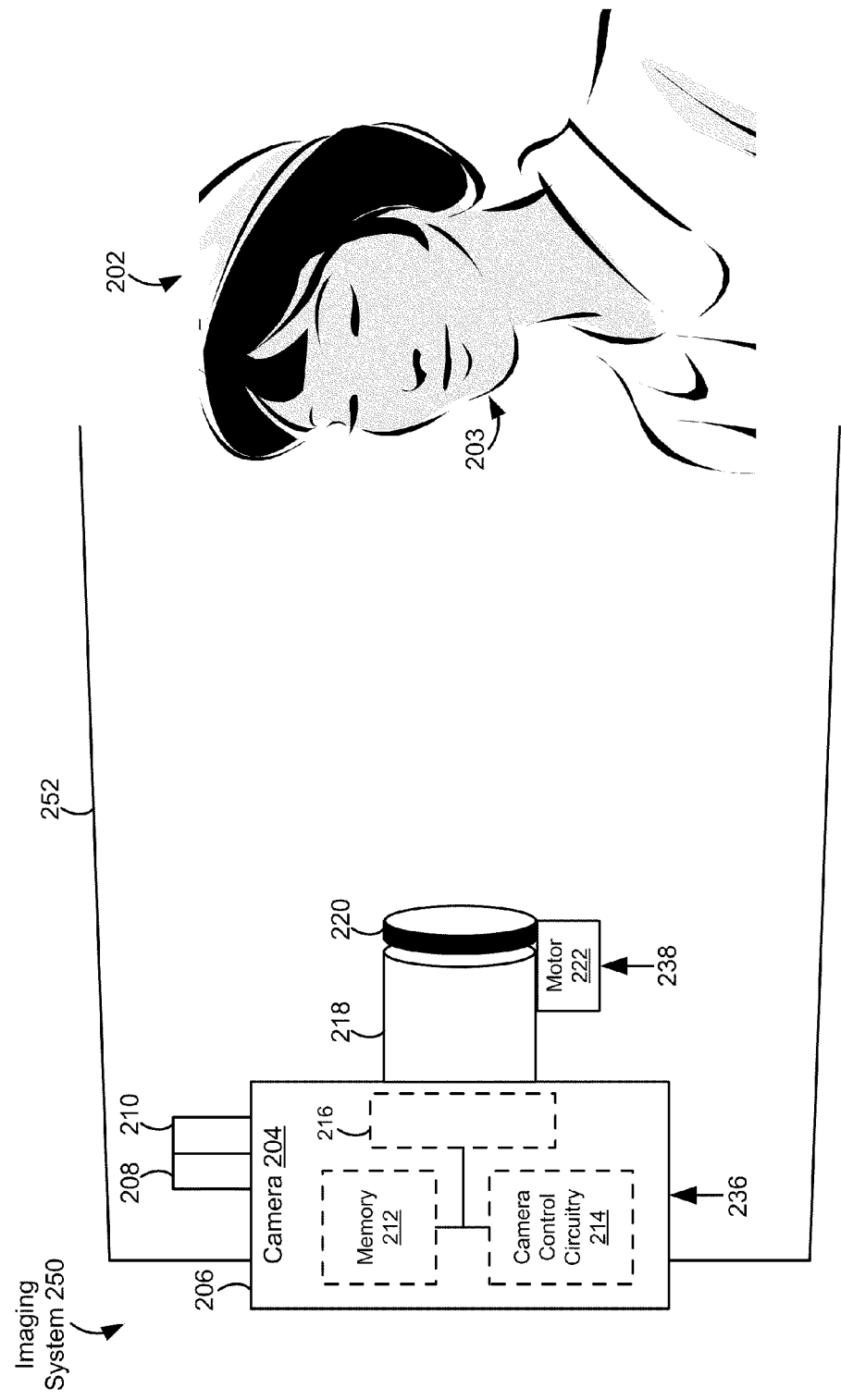

In some embodiments, the imaging control module 820 includes a polarizer control module 822 for automatically controlling an adjustable polarizer (e.g., for controlling the motor 222 via the control board 224, FIG. 2A) and/or an image acquisition module 824 for controlling image acquisition (e.g., using a camera 204, FIGS. 2A-2C).

In some embodiments, the image processing module 826 includes an image subtraction module 828 for subtracting respective acquired images (e.g., in accordance with operations 712 (FIG. 7A), 746 (FIG. 7D) or 768 (FIG. 7E)). In some embodiments, the image processing module 826 includes an image calibration module 832.88

Each of the above identified elements in FIG. 8 may be stored in one or more of the previously mentioned memory devices. Each of the above-identified modules corresponds to a set of instructions for performing a function described above. These sets of instructions need not be implemented as separate software programs, procedures or modules. Various subsets of the above-identified modules may be combined or otherwise re-arranged in various embodiments. In some embodiments, memory 804 may store a subset of the modules and data structures identified above. Furthermore, memory 804 may store additional modules and data structures not described above.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of generating a sub-surface skin image, comprising:

at a system having a memory and one or more processor for processing and displaying images of skin:

illuminating a subject with polarized light having a first polarization;

setting an adjustable polarizer to a first setting to admit light having the first polarization onto a photodetector and otherwise reject light;

with the adjustable polarizer in the first setting, using the photodetector to acquire a first image of the illuminated subject;

setting the adjustable polarizer to a second setting to at least partially reject light having the first polarization and to at least partially admit light having polarization distinct from the first polarization onto the photodetector;

with the adjustable polarizer in the second setting, using the photodetector to acquire a second image of the illuminated subject; and subtracting the first image from the second image to generate a third image of the subject.

2. The method of claim 1, further comprising:

performing computerized analysis of the third image to determine a skin color of the subject; and using the skin color to automatically select a recommended cosmetic product.

3. The method of claim 2, further comprising:

transmitting instructions to an automated cosmetic formulation system to produce the recommended cosmetic product.

4. The method of claim 1, further comprising:

performing computerized analysis of the third image to identify a skin feature in the third image; and performing an automated comparison of the identified skin feature to a corresponding skin feature in a stored historical image.

5. The method of claim 1, further comprising:

calibrating the photodetector; and correcting the first and second images in accordance with the calibration.

6. A computer-implemented method of processing and displaying images of skin, comprising:

at a system having a memory and one or more processor for processing and displaying images of skin:

receiving a first image of a subject, the first image having been acquired at an optical apparatus with the subject illuminated with light having a first polarization and the optical apparatus configured to receive light having the first polarization and to otherwise reject light;

receiving a second image of the subject, the second image having been acquired at the optical apparatus with the subject illuminated with light having the first polarization and the optical apparatus configured to at least partially reject light having the first polarization and to at least partially receive light having polarization distinct from the first polarization;

subtracting the first image from the second image to generate a third image of the subject; and displaying the third image.

7. A system for processing and displaying images of skin, comprising:

memory;

a display;

one or more processors; and one or more programs stored in the memory and configured for execution by the one or more processors, the one or more programs including:

instructions to receive a first image of a subject, the first image having been acquired at an optical apparatus with the subject illuminated with light having a first polarization and the optical apparatus configured to receive light having the first polarization and to otherwise reject light;

instructions to receive a second image of the subject, the second image having been acquired at the optical apparatus with the subject illuminated with light having the first polarization and the optical apparatus configured to at least partially reject light having the first polarization and to at least partially receive light having polarization distinct from the first polarization;

instructions to subtract the first image from the second image to generate a third image of the subject; and instructions to display the third image.

8. A computer readable storage medium storing one or more programs configured to be executed by a computer system to process and display images of skin, the one or more programs comprising:

instructions to receive a first image of a subject, the first image having been acquired at an optical apparatus with the subject illuminated with light having a first polarization and the optical apparatus configured to receive light having the first polarization and to otherwise reject light;

instructions to receive a second image of the subject, the second image having been acquired at the optical apparatus with the subject illuminated with light having the first polarization and the optical apparatus configured to at least partially reject light having the first polarization and to at least partially receive light having polarization distinct from the first polarization;

instructions to subtract the first image from the second image to generate a third image of the subject; and instructions to display the third image.

\* \* \* \* \*